United States Patent
Kent et al.

(10) Patent No.: US 12,383,322 B2
(45) Date of Patent: Aug. 12, 2025

(54) METHODS AND DEVICES FOR SYNDESMOSIS TENSIONING

(71) Applicant: DePuy Synthes Products, Inc., Raynham, MA (US)

(72) Inventors: Todd Kent, Raynham, MA (US); Daniel Sayger, Memphis, TN (US)

(73) Assignee: DePuy Synthes Products, Inc., Raynham, MA (US)

( * ) Notice: Subject to any disclaimer, the term of this patent is extended or adjusted under 35 U.S.C. 154(b) by 205 days.

(21) Appl. No.: 18/453,784

(22) Filed: Aug. 22, 2023

(65) Prior Publication Data
US 2025/0064496 A1    Feb. 27, 2025

(51) Int. Cl.
    *A61B 17/88*    (2006.01)
(52) U.S. Cl.
    CPC ............... *A61B 17/8866* (2013.01)
(58) Field of Classification Search
    CPC ............ A61B 17/8866; A61B 17/8875; A61B 2017/0409; A61B 2017/0496
    See application file for complete search history.

(56) References Cited

U.S. PATENT DOCUMENTS

| | | | |
|---|---|---|---|
| 5,306,290 | A | 4/1994 | Martins et al. |
| 6,187,008 | B1 * | 2/2001 | Hamman ........... A61B 17/8888 606/232 |
| 7,029,490 | B2 | 4/2006 | Grafton et al. |
| 7,235,091 | B2 | 6/2007 | Thornes |
| 7,608,098 | B1 * | 10/2009 | Stone ................. A61F 2/0805 606/304 |
| 7,611,521 | B2 | 11/2009 | Lubbers et al. |
| 7,955,388 | B2 * | 6/2011 | Jensen ............... A61B 17/8685 623/13.14 |
| 8,298,247 | B2 | 10/2012 | Sterrett et al. |
| 8,398,678 | B2 | 3/2013 | Baker et al. |
| 8,460,379 | B2 | 6/2013 | Albertorio et al. |
| | | (Continued) | |

FOREIGN PATENT DOCUMENTS

| | | |
|---|---|---|
| CN | 108186096 A | 6/2018 |
| EP | 3206607 B1 | 5/2018 |
| RU | 2461366 C1 | 9/2012 |

OTHER PUBLICATIONS

International Search Report and Written Opinion dated Nov. 19, 2024, from corresponding International Application No. PCT/IB2024/057626.

*Primary Examiner* — Amy R Sipp

(57) ABSTRACT

A system is provided for the approximation of two bones. The system may include an implant having a first anchor, a flexible segment, and a second anchor. The first anchor may be configured for insertion into a first bone. The second anchor may be configured to engage with a second bone. The flexible segment may extend between the first and second anchors. The system may include a delivery device which may include a removable driver configured to facilitate insertion of the first anchor into the first bone, and a first handle configured to engage the removeable driver. The delivery device may include a second handle configured to increase tension on the flexible segment. The delivery device may include a third handle configured to engage the second anchor with the second bone and to attach the flexible segment to the second anchor.

18 Claims, 14 Drawing Sheets

(56) References Cited

U.S. PATENT DOCUMENTS

| | | |
|---|---|---|
| 8,888,779 B2 | 11/2014 | Senn et al. |
| D740,417 S | 10/2015 | Chavan |
| D740,418 S | 10/2015 | Chavan et al. |
| D740,419 S | 10/2015 | Chavan et al. |
| D740,480 S | 10/2015 | Thompson |
| 9,179,950 B2 | 11/2015 | Zajac et al. |
| 9,421,049 B2 | 8/2016 | Rogachefsky |
| 9,737,347 B2 | 8/2017 | Schlienger et al. |
| 9,788,876 B2 * | 10/2017 | Stone ................ A61B 17/0401 |
| 9,826,969 B2 | 11/2017 | Larsen |
| 9,888,916 B2 | 2/2018 | Bonutti et al. |
| 9,943,304 B2 | 4/2018 | Branthover et al. |
| 10,130,377 B2 | 11/2018 | Hollis et al. |
| 10,206,670 B2 | 2/2019 | Thornes |
| 10,251,686 B2 | 4/2019 | Zajac et al. |
| 10,327,826 B2 | 6/2019 | Horrell et al. |
| 10,390,816 B2 | 8/2019 | Thornes |
| 10,405,847 B2 | 9/2019 | Petry et al. |
| 10,413,341 B2 | 9/2019 | Chaudot et al. |
| 10,492,774 B2 | 12/2019 | Larsen |
| 10,499,900 B2 | 12/2019 | Wade |
| 10,499,972 B2 | 12/2019 | Bosshard et al. |
| 10,582,957 B2 | 3/2020 | Hollis et al. |
| 10,682,131 B2 | 6/2020 | Fallin et al. |
| 10,695,049 B2 | 6/2020 | Thornes |
| 10,722,229 B2 | 7/2020 | O'Donnell et al. |
| 10,736,622 B2 | 8/2020 | Thornes |
| 10,799,250 B2 | 10/2020 | Hollis et al. |
| 10,864,028 B2 | 12/2020 | Zajac et al. |
| 10,918,375 B2 | 2/2021 | Thornes |
| 11,109,855 B2 | 9/2021 | Shoshtaev et al. |
| 11,129,654 B2 | 9/2021 | Zajac et al. |
| 11,234,688 B2 | 2/2022 | Taber et al. |
| 11,253,301 B2 | 2/2022 | Larsen et al. |
| 11,471,146 B2 | 10/2022 | Petry et al. |
| 11,534,157 B2 | 12/2022 | Norton |
| 2006/0100627 A1 * | 5/2006 | Stone .................... A61F 2/0805 |
| | | 606/907 |
| 2011/0112576 A1 * | 5/2011 | Nguyen ............. A61B 17/0401 |
| | | 606/232 |
| 2011/0282361 A1 * | 11/2011 | Miller ................ A61B 17/0401 |
| | | 606/139 |
| 2012/0172936 A1 * | 7/2012 | Horrell ............... A61B 17/0401 |
| | | 606/104 |
| 2013/0331897 A1 * | 12/2013 | Holt .................... A61B 17/1684 |
| | | 606/328 |
| 2014/0194907 A1 * | 7/2014 | Bonutti .............. A61B 17/0401 |
| | | 606/151 |
| 2016/0038186 A1 * | 2/2016 | Herzog ................ A61B 17/686 |
| | | 606/328 |
| 2016/0287302 A1 * | 10/2016 | Horrell ................... A61B 17/84 |
| 2017/0035552 A1 * | 2/2017 | Fallin ............. A61B 17/06133 |
| 2017/0128061 A1 | 5/2017 | Stone et al. |
| 2018/0049784 A1 | 2/2018 | Gault et al. |
| 2018/0098762 A1 * | 4/2018 | Borden ............. A61B 17/0401 |
| 2020/0245997 A1 * | 8/2020 | Balboa .............. A61B 17/0401 |
| 2021/0059729 A1 | 3/2021 | Zajac et al. |
| 2021/0161518 A1 | 6/2021 | Thornes |
| 2021/0219972 A1 | 7/2021 | Zakhary |
| 2022/0000470 A1 * | 1/2022 | Fallin ................ A61B 17/0401 |
| 2022/0071676 A1 * | 3/2022 | Horrell ............. G06Q 20/3678 |
| 2022/0142635 A1 | 5/2022 | Bachmaier et al. |
| 2022/0151604 A1 * | 5/2022 | Fallin ............... A61B 17/1604 |
| 2022/0192817 A1 * | 6/2022 | Gill ........................ A61B 17/72 |
| 2022/0226100 A1 * | 7/2022 | Feuer ................. A61B 17/8645 |
| 2022/0323058 A1 | 10/2022 | Zenz-Olson et al. |
| 2023/0248351 A1 * | 8/2023 | Khalil ................ A61B 17/0401 |
| | | 606/232 |
| 2023/0320838 A1 * | 10/2023 | Duquesnel ......... A61B 17/0401 |
| | | 623/13.12 |
| 2024/0315830 A1 * | 9/2024 | Johnson ................ A61F 2/0811 |
| 2024/0415545 A1 * | 12/2024 | Colwell ............. A61B 17/0401 |

* cited by examiner

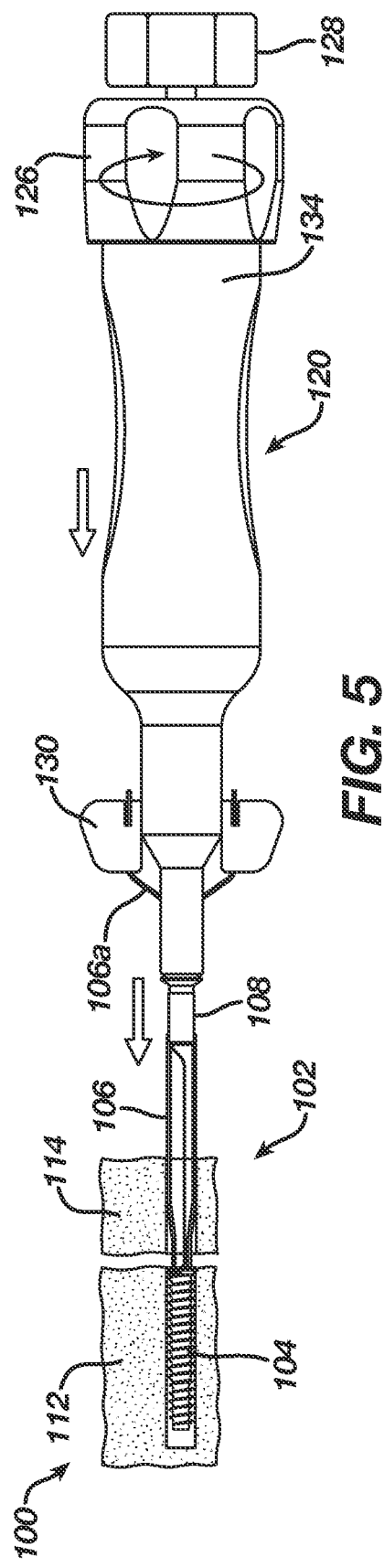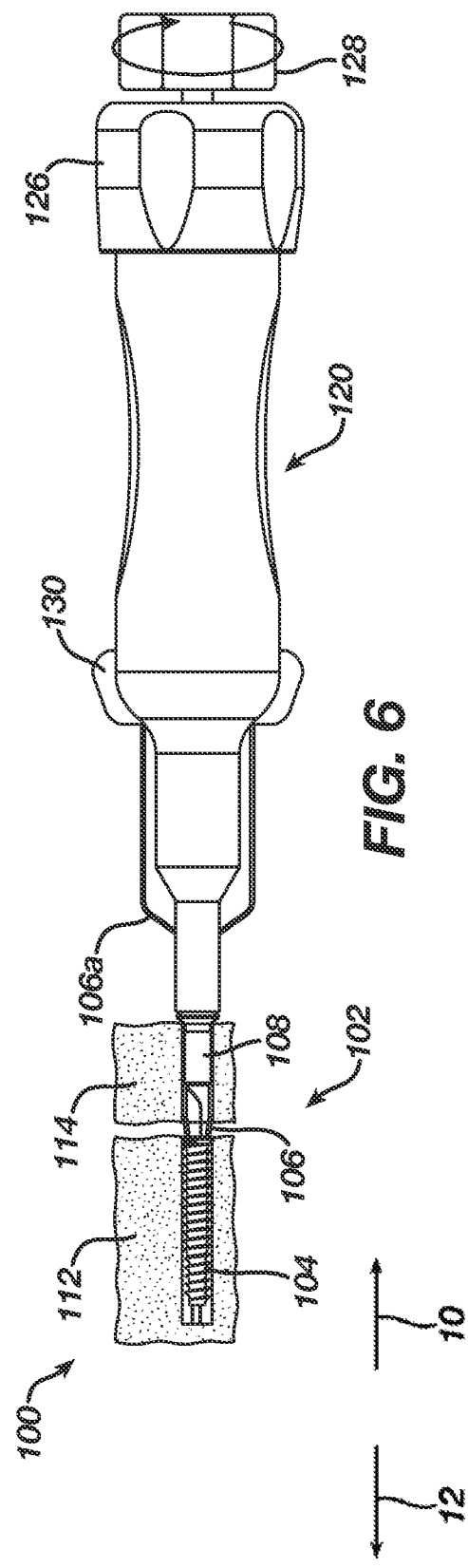
FIG. 5
FIG. 6

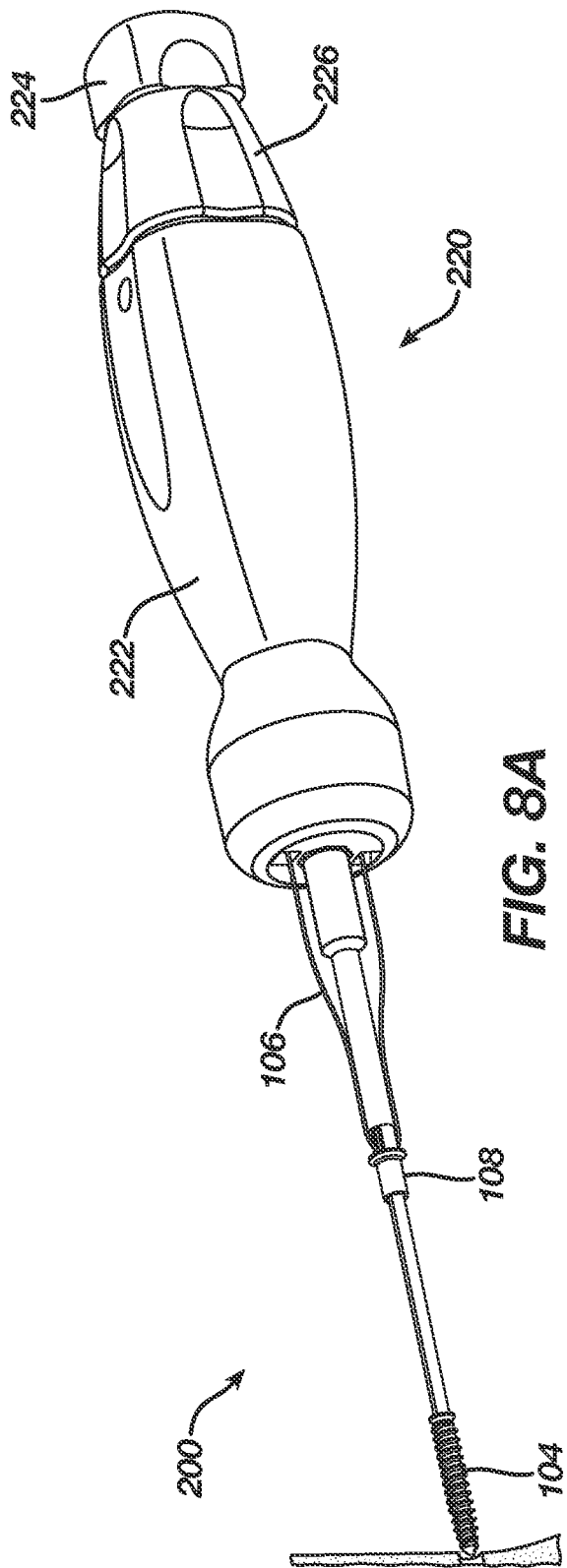
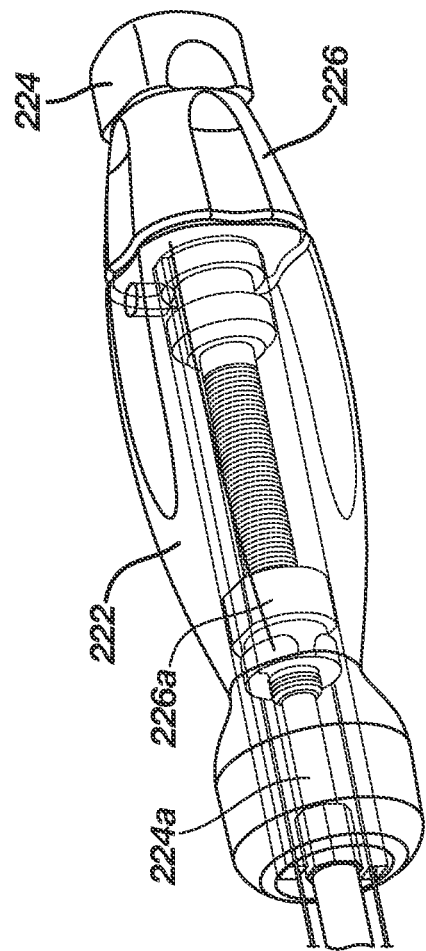
FIG. 8A
FIG. 8B

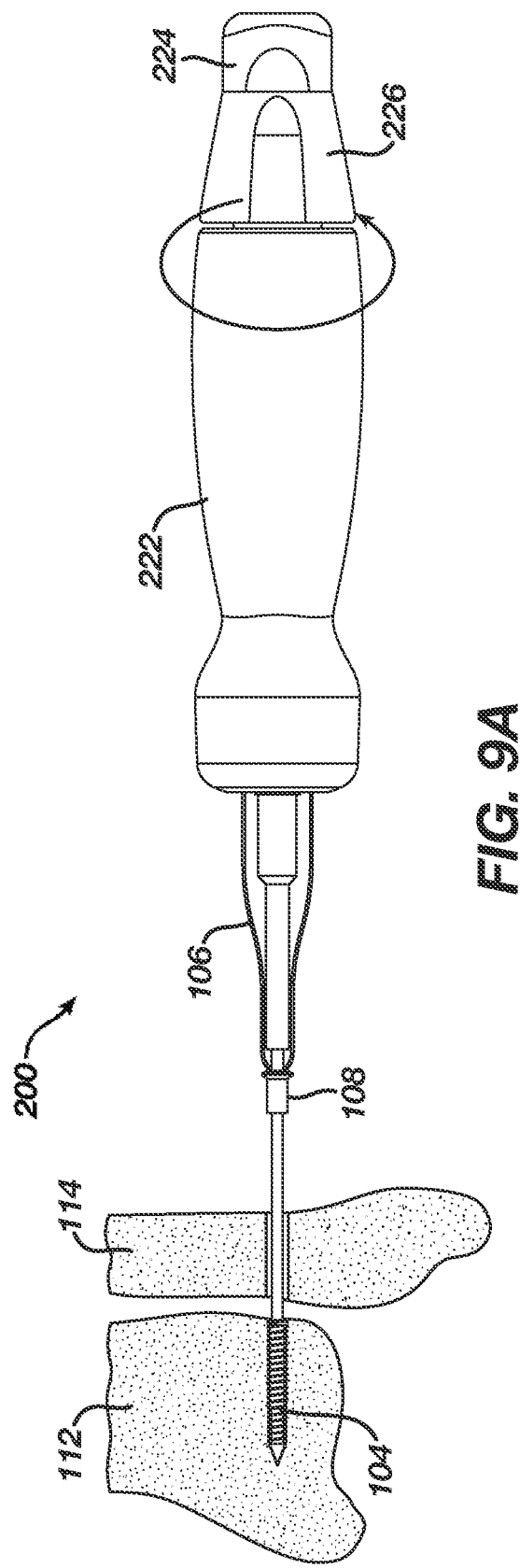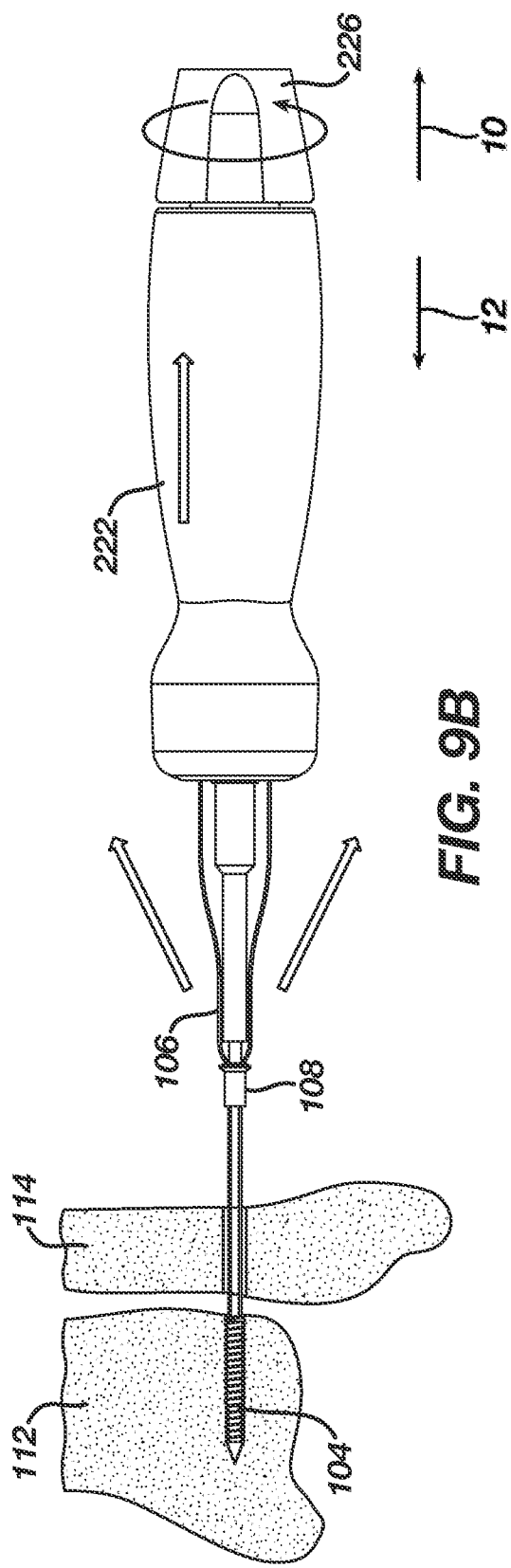
FIG. 9A
FIG. 9B

300

┌─────────────────────────────────────────────────────────┐
│ Delivering, via a first handle and a removeable driver of a │
│ delivery device, a first anchor into a first bone, wherein the │ —302
│ first anchor engages with a distal end of a flexible segment │
└─────────────────────────────────────────────────────────┘
                              ↓
┌─────────────────────────────────────────────────────────┐
│ Disengaging the removeable driver from the delivery device, │ —304
│          thereby exposing the flexible segment          │
└─────────────────────────────────────────────────────────┘
                              ↓
┌─────────────────────────────────────────────────────────┐
│       Adjusting, via a second handle of the delivery device, │
│    tension of the flexible segment by pulling one or more   │ —306
│  proximal ends of the flexible segment in a proximal direction │
└─────────────────────────────────────────────────────────┘
                              ↓
┌─────────────────────────────────────────────────────────┐
│    Delivering, via a third handle of the delivery device, a  │ —308
│           second anchor into a second bone              │
└─────────────────────────────────────────────────────────┘
                              ↓
┌─────────────────────────────────────────────────────────┐
│   Attaching, via the third handle of the delivery device, the │ —310
│         flexible segment to the second anchor           │
└─────────────────────────────────────────────────────────┘

*FIG. 11*

METHODS AND DEVICES FOR SYNDESMOSIS TENSIONING

FIELD

The present invention generally relates to methods and devices for syndesmosis tensioning. More specifically, certain embodiments relate to methods and devices for tensioning of the tibia and fibula following an injury to the corresponding syndesmotic joint.

BACKGROUND

A syndesmotic injury results when a traumatic injury damages the ligaments that span the gap between the distal tibia and fibula. This can be the result of a high ankle sprain, with no fracture of the fibula, or can also accompany a fibular fracture in a Weber B or Weber C fracture.

A surgeon can determine the presence of a syndesmotic injury by direct visualization of the joint or through radiographic imaging while positioning the ankle in a mortise view orientation. In either case, loads are applied to the joint in either a direct lateral load applied to the fibula or by applying an external rotation load to the foot. While the load is being applied, the relative distance between the fibula and the tibia, the fibula and the talus, and the tibia and the talus are observed to determine the level of damage sustained by the ligaments that typically hold the syndesmotic joint together.

If a syndesmotic injury is found to be present, the typical treatment involves stabilizing the fibula and tibia with respect to each other in the proper orientation and holding them there throughout the soft tissue healing period to allow the ligaments to re-attach and heal. In the event of a syndesmotic injury with a corresponding fibula fracture, this is done while also stabilizing the fibular fracture, which is usually accomplished with a small fracture plate on the lateral side of the fibula. Traditionally the method of stabilization has been to place one or more cortical screws across the syndesmosis, with the head against the lateral face of the fibula and the tip of the screw being in the middle of the tibia or in the medial cortex of the tibia.

This form of treatment provides very rigid fixation, allowing the ligaments to heal, but makes return to weight-bearing more difficult. During a standard gait, the ligaments hold the distance between the tibia and fibula fairly constant, but allow a small amount of shear motion and rotation of the fibula with respect to the tibia. The presence of the fixation screws prevents this motion and can cause discomfort and limited flexibility of the ankle joint. Typically, the surgeon prescribes a secondary surgery to remove the screws once the ligaments have healed. In some cases, a surgeon may simply recommend a return to weight-bearing when the ligaments have healed and, after a period of time of loading the screws, they will experience a fatigue failure and normal anatomical motion will be restored.

To address these rigidity issues, some methods of stabilization have been developed to include a flexible internal segment connected by a first anchor on the lateral side of the fibula and a second anchor on the medial side of the tibia. These methods, however, typically present challenges in achieving an appropriate degree of tension between the two bones for sufficient healing and recovery.

Accordingly, alternative devices and methods for providing syndesmosis tensioning would be useful.

SUMMARY

The present invention is directed to methods and devices for providing syndesmosis tensioning while stabilizing a joint between two bones, e.g., the tibia and fibula, during a healing period following a traumatic injury.

An example system is provided for the approximation of two bones. The system may include an implant having a first anchor, a flexible segment, and a second anchor. The first anchor may include a distal end configured for insertion into a first hole in a first bone. The second anchor may be configured to engage with a second bone. The flexible segment may extend between the first and second anchors. The system may further include a delivery device configured to engage the implant with the first and second bones. The delivery device may include a removable driver configured to engage the first anchor to facilitate insertion of the first anchor into the first hole. The delivery device may include a first handle configured to engage the removeable driver to facilitate insertion of the first anchor into the first hole by the removable driver. The delivery device may include a second handle coupled to the first handle and configured, with the removable driver disengaged from the first handle and first anchor, to increase tension on the flexible segment by pulling one or more proximal ends of the flexible segment in a proximal direction. The delivery device may include a third handle configured to engage the second anchor with the second bone and to attach the flexible segment to the second anchor.

An example method is provided for the approximation of two bones. The method may include delivering, via a first handle and a removeable driver of a delivery device, a first anchor into a first bone, wherein the first anchor engages with a distal end of a flexible segment. The method may include disengaging the removeable driver from the delivery device, thereby exposing the flexible segment. The method may include adjusting, via a second handle of the delivery device, tension of the flexible segment by pulling one or more proximal ends of the flexible segment in a proximal direction. The method may include delivering, via a third handle of the delivery device, a second anchor into a second bone. The method may include attaching, via the third handle of the delivery device, the flexible segment to the second anchor.

An example method is provided for constructing a system for the approximation of two bones. The method may include coupling a locking component to a third handle of a delivery device. The method may include feeding a flexible segment through a second anchor of an implant. The method may include configuring the delivery device such that rotation of the third handle couples the locking component to the flexible segment and the second anchor. The method may include coupling a proximal end of a flexible segment to a second handle of the delivery device such that a distal end of the flexible segment is coupled to a first anchor of the implant. The method may include configuring the delivery device such that rotation of the second handle adjusts tension in the flexible segment. The method may include engaging a distal end of a removable driver to a proximal end of the first anchor and engaging a proximal end of the removable driver to a first handle of the delivery device such that the flexible segment extends along the removable driver. The method may include configuring the delivery device such that rotation of the first handle rotates the removable driver and thereby the first anchor. The method may include configuring the delivery device such that the removable driver is configured to be disengaged from the first handle and the first anchor while the flexible segment remains coupled to the second handle and the first anchor.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 5 is a cross-sectional view of a tibia and fibula showing an example step of an example method for installing an implant, such as that shown in FIG. 1, according to aspects of the present invention.

FIG. 6 is a cross-sectional view of a tibia and fibula showing an example step of an example method for installing an implant, such as that shown in FIG. 1, according to aspects of the present invention.

FIG. 8A is a perspective view of an example delivery device used for installing an implant, such as that shown in FIG. 1, according to aspects of the present invention.

FIG. 8B is a cross-sectional view of components of the example delivery device of FIG. 8A, according to aspects of the present invention.

FIG. 9A is a cross-sectional view of a tibia and fibula showing an example step of an example method for installing an implant, such as that shown in FIG. 1, according to aspects of the present invention.

FIG. 9B is a cross-sectional view of a tibia and fibula showing an example step of an example method for installing an implant, such as that shown in FIG. 1, according to aspects of the present invention.

FIG. 11 is a flowchart of an example method for providing syndesmosis tensioning, according to aspects of the present invention.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 80%" may refer to the range of values from 60% to 100%.

The example devices and methods of treatment described herein generally involve providing syndesmosis tensioning and repair of two bones, such as the tibia and fibula bones. That is, a delivery device having one or more handles may be used to install an implant into two bones, such as the tibia and fibula bones, to provide an appropriate degree of tensioning between the two bones for injury treatment and repair.

Various example systems and methods are presented herein. Features from each example are combinable with other examples as understood by persons skilled in the pertinent art.

Figure 1:
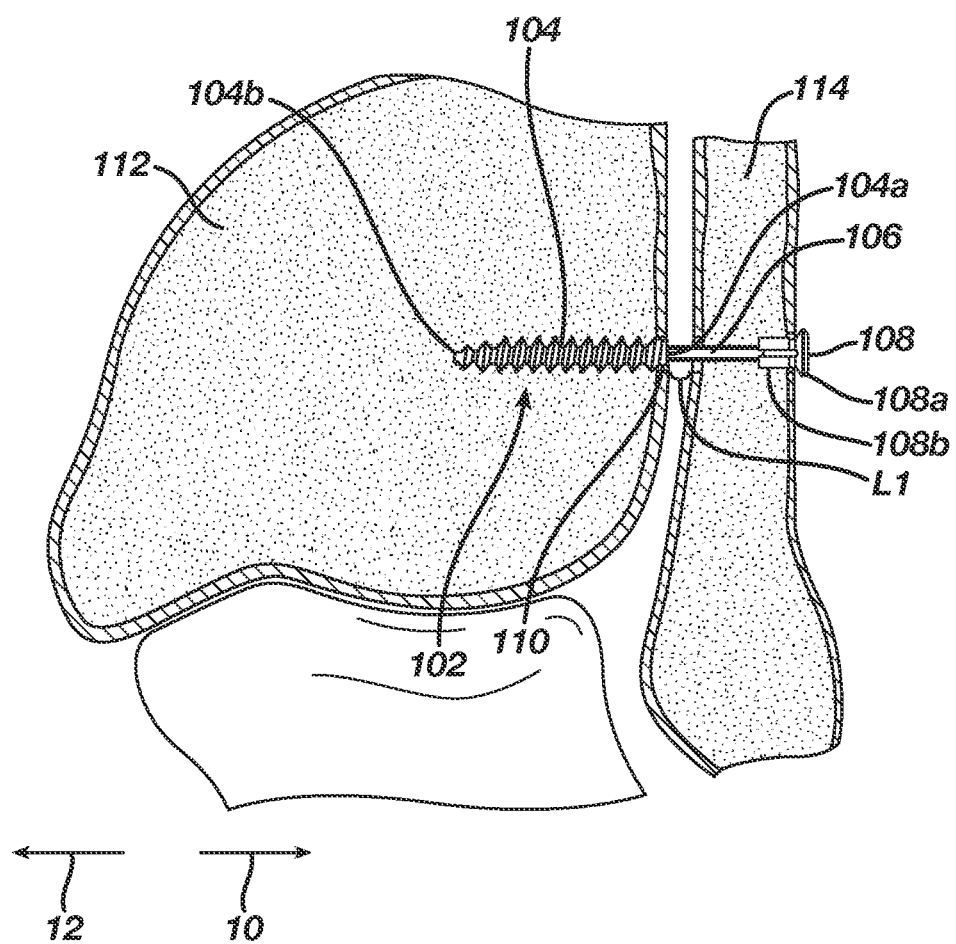
FIG. 1 is an illustration of an example implant used for syndesmosis tensioning, according to aspects of the present invention.

FIG. 1 is an illustration of an example implant 102 for the approximation of two bones. The implant 102 may include a first anchor 104, which may include a proximal end 104a and a distal end 104b. The first anchor 104 may be configured to be inserted into a first bone 112 (e.g., a tibia bone) through a first bone hole 110. In some embodiments, the implant 102 may further include a second anchor 108 configured to engage a second bone 114 (e.g., a fibula bone). The second anchor 108 may include a proximal end 108a and a distal end 108b, and may be configured to be inserted into the second bone 114. The second anchor 108 may include a threaded screw, a barbed fastener, a button, and/or a cap.

The first and/or second anchors 104, 108 can include any type of suture anchor, and can be manufactured from a surgical stainless steel or other suitable biocompatible material, such as 316 LVM stainless steel, titanium, and other suitable materials, such as nitinol, bio-absorbables, or non-absorbables. First and/or second anchors 104, 108 can also include an "all-textile" anchor.

Figure 2:
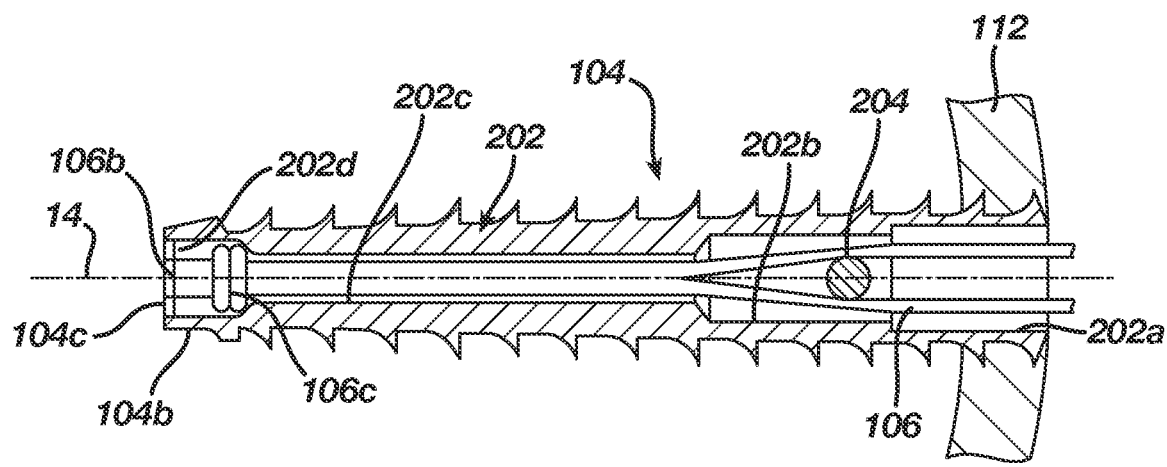
FIG. 2 is a cross-sectional view of a first anchor of the example implant of FIG. 1, according to aspects of the present invention.

As particularly shown in FIG. 2, the first anchor 104 may include a bore 202 extending from the proximal end 104a at least partially towards the distal end 104b, generally along a longitudinal axis 14 of the implant 102. The bore 202 can include a proximal region 202a, an intermediate region 202b distal to the proximate region 202a including a first support structure 204 therein, and a distal region 202c extending distally from the intermediate region 202b to a recess 202d in the distal tip 104c. The intermediate region 202b and distal region 202c may have a circular or other desired cross-sectional shape, with the distal region 202c having a diameter or other maximum cross-section smaller than the intermediate region 202b. The recess 202d may have a diameter or other cross-section larger than the distal region 202c, e.g., to receive a knot 106c or otherwise fixed distal ends 106b (e.g., a crimp eyelet pin, etc.) of the flexible segment 106, as described elsewhere herein.

A first support structure 204 may be provided within the bore 202, e.g., across the intermediate region 202b substantially perpendicular to the longitudinal axis 14. In one example first anchor 104, holes may be provided through opposite side walls of the first anchor 104 into the intermediate region 202b and a first support structure 204, e.g., a pin, may be inserted into the holes such that the first support structure 204 extends across the intermediate region 202b and substantially permanently attached thereto, e.g., by one or more of press-fit or other interference fit, bonding with adhesive, sonic welding, soldering, and the like. In an alternative example first anchor 104, the holes may be omitted and a first support structure 204 may be inserted through the intermediate region 202b and positioned and fixed across the intermediate region 202b, e.g., by one or more of interference fit, bonding with adhesive, sonic welding, soldering, and the like. In another example first anchor 104, a support structure may be integrally formed with the first anchor 104, e.g., machined, cast, molded, and the like from the same piece of material as the rest of the first anchor 104. The pin or other first support structure 204 generally has a diameter or other cross-section smaller than the intermediate region 202b such that a flexible segment 116 may be wrapped at least partially around the first support structure 204, as described further elsewhere herein.

Turning back to FIG. 1, in some embodiments, the implant 102 may include a flexible segment 106 configured to extend between the first and second anchors, 104, 108, as further discussed below. The flexible segment 106 may be configured to adjust a distance L1 between the first and second bones 112, 114.

The flexible segment 106 can be manufactured out of a variety of fibers or filaments including but not limited to polymer filaments, metallic filaments, or organic filaments, or other filaments such as carbon fiber or carbon nanotubes, etc., and can be made of resorbable and/or biologic materials. Flexible segment 106 can include, but is not limited to, a coreless suture, a suture with a jacket and a central core, a tape, or any other tension member available or contemplated, can be poly-coated or uncoated, and can include collagen.

FIGS. 3-6 provide an example system 100 for the approximation and tensioning of two bones, such as the tibia and fibula bones, and an example method for delivering an implant 102, such as that shown in FIG. 1, into the two bones. It will be appreciated that the apparatus, systems, and methods described herein may also be used in other locations and/or procedures, e.g., to provide approximation between two bones other than the tibia and fibula.

Figure 3:
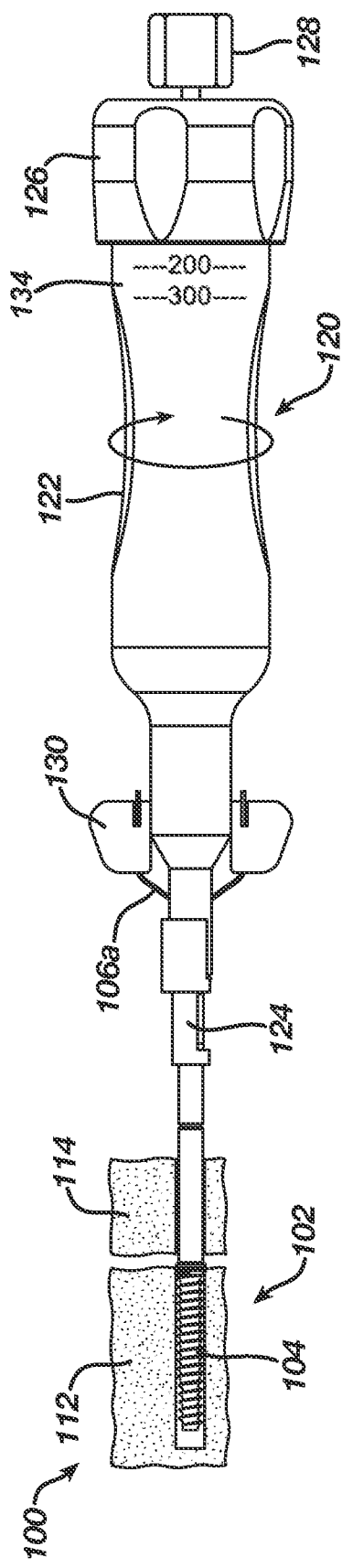
FIG. 3 is a cross-sectional view of a tibia and fibula showing an example step of an example method for installing an implant, such as that shown in FIG. 1, according to aspects of the present invention.
Figure 4:
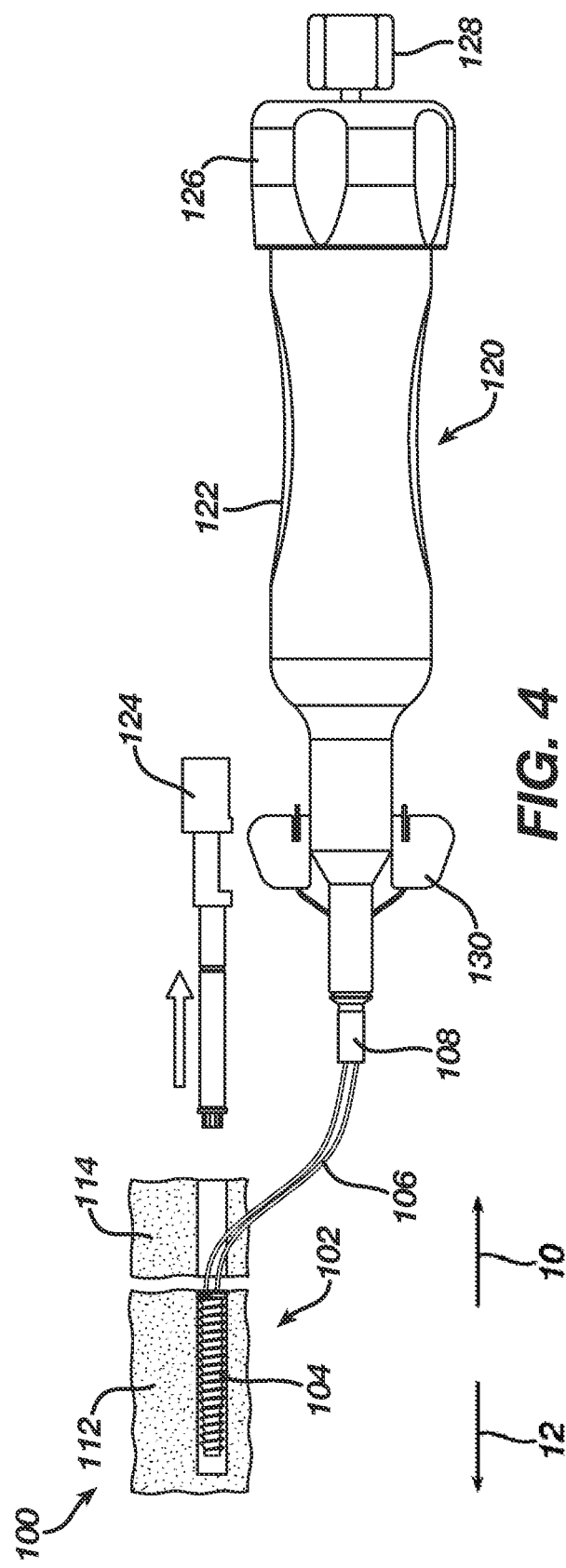
FIG. 4 is a cross-sectional view of a tibia and fibula showing an example step of an example method for installing an implant, such as that shown in FIG. 1, according to aspects of the present invention.

The system 100 may include an implant 102, such as that shown in FIG. 1, and a delivery device 120. The delivery device 120 may include a removeable driver 124 (FIGS. 3-4) configured to facilitate insertion of the first anchor 104 into the first hole 110 of the first bone 112. The delivery device 120 may further include a first handle 122 configured to engage the removeable driver 124 to facilitate insertion of the first anchor 104 into the first hole 110 by the removable driver 124. For example, as shown in FIGS. 3-4, the removeable driver 124 may first be used to facilitate insertion of the first anchor 104 into the first bone 112, such as by rotating the first handle 122 thereby rotating the removable driver 124 and the first anchor 104. The first anchor 104 may then be inserted into, e.g., screwed into, the first bone 112.

Figure 4A:
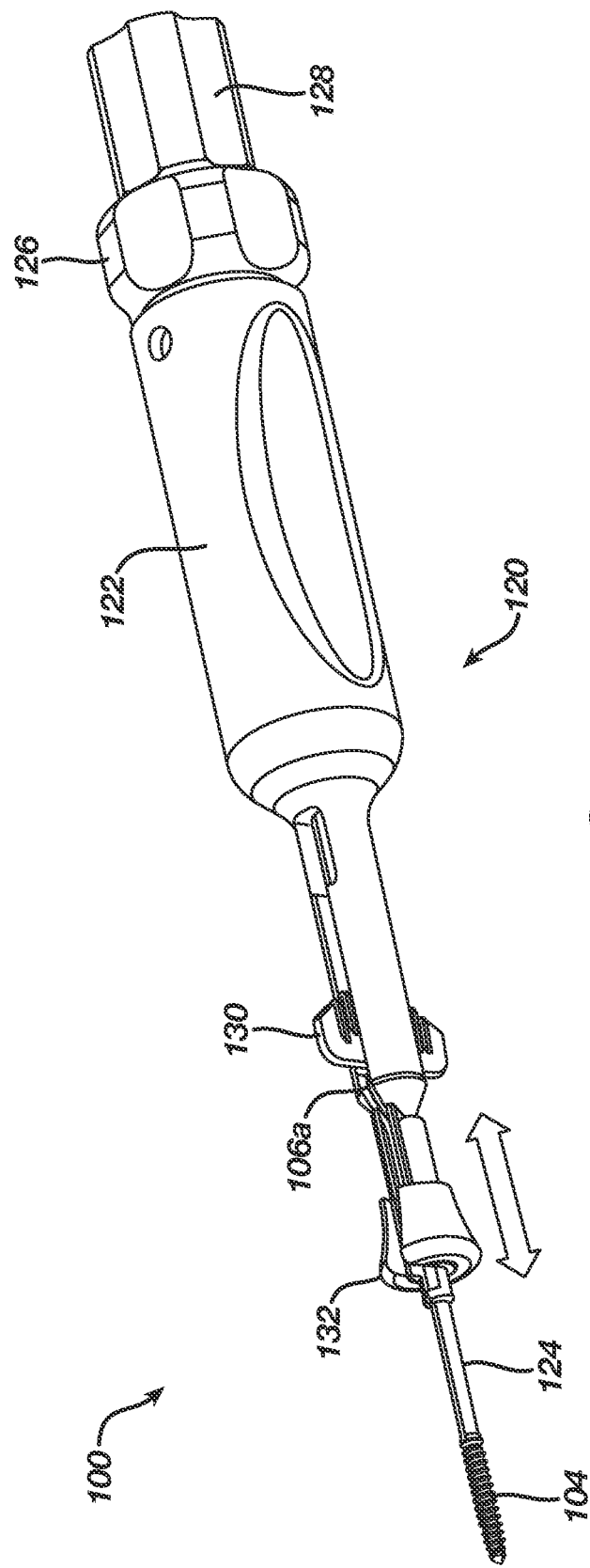
FIG. 4A is a perspective view of an example delivery device used for installing an implant, such as that shown in FIG. 1, according to aspects of the present invention.

As shown in FIG. 4, once the first anchor 104 has been inserted into and anchored in the first bone 112, the removeable driver 124 may be removed from the delivery device 120, thereby exposing the flexible segment 106 extending between the first anchor 104 and the second anchor 108, which itself is engaged with the delivery device 120. In some embodiments, as shown in FIG. 4A, the delivery device 120 may include a slider 132 configured to slide along a length of the removeable driver 124 thereby enabling the removable driver 124 to disengage from the delivery device 120.

As particularly shown in FIGS. 5-6, the delivery device 120 may further include a second handle 126 coupled to the first handle 122. In some embodiments, the second handle 126 may be rotatable independent of the first handle 122. In some embodiments, the second handle 126 may be configured, with the removable driver 124 disengaged from the first handle 122 and first anchor 104, to increase tension on the flexible segment 106 by pulling one or more proximal ends 106a of the flexible segment 106 in a proximal direction 10. In some embodiments, the delivery device 120 may include one or more extensions 130 configured to engage with the proximal ends 106a of the flexible segment 106, whereby rotation of the second handle 126 is configured to move the extensions 130 proximally along a length of the delivery device 120 thereby increasing the tension on the flexible segment 106, as shown in FIG. 6.

In some embodiments, the delivery device 120 may include a force gauge 134 (FIG. 3) that may provide an indication of the tensile force placed on the flexible segment 106 as the second handle 126 is rotated and the tension of the flexible segment 106 is adjusted.

As particularly shown in FIG. 6, the delivery device 120 may further include a third handle 128 configured to engage the second anchor 108 with the second bone 114 and to attach the flexible segment 106 to the second anchor 108. For example, rotation of the third handle 128 (e.g., independent of the first handle 122 and second handle 126) may provide for the second anchor 108 being locked or fitted into place within the second bone 114, and the proximal ends 106a of the flexible segment 106 being attached to the second anchor 108 with a desired amount of tension.

Figure 7A:
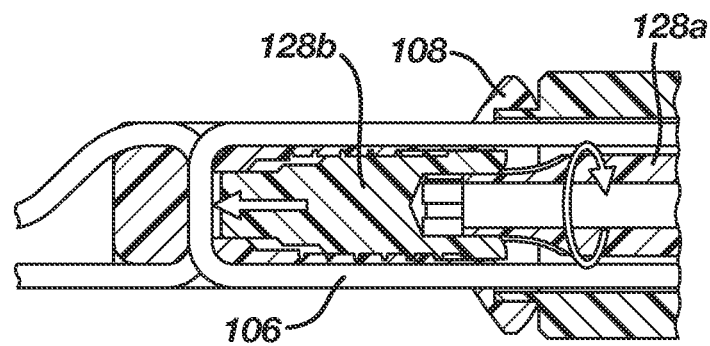
FIG. 7A is a cross-sectional view of an engagement between a second anchor and a flexible segment of an example implant, such as that shown in FIG. 1, according to aspects of the present invention.
Figure 7B:
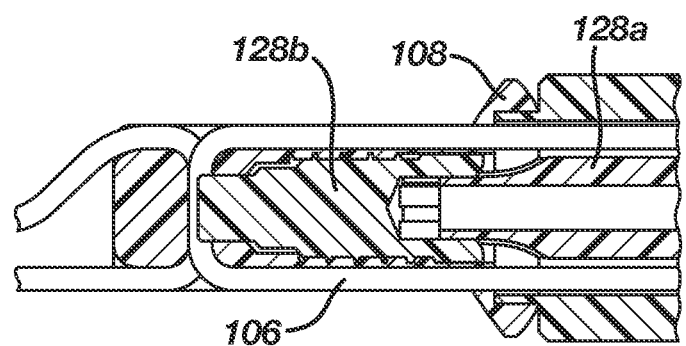
FIG. 7B is a cross-sectional view of an engagement between a second anchor and a flexible segment of an example implant, such as that shown in FIG. 1, according to aspects of the present invention.
Figure 7C:
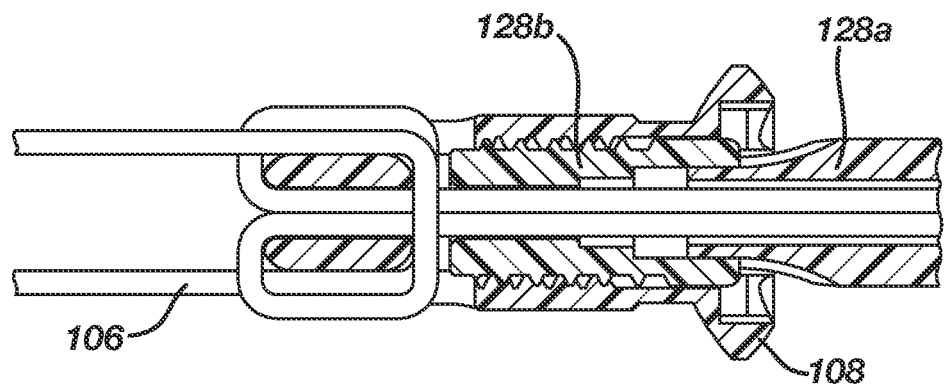
FIG. 7C is a cross-sectional view of an engagement between a second anchor and a flexible segment of an example implant, such as that shown in FIG. 1, according to aspects of the present invention.
Figure 7E:
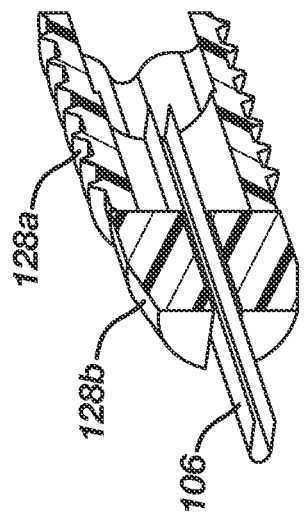
FIG. 7E is a cross-sectional view of an engagement between a second anchor and a flexible segment of an example implant, such as that shown in FIG. 1, according to aspects of the present invention.
Figure 7G:
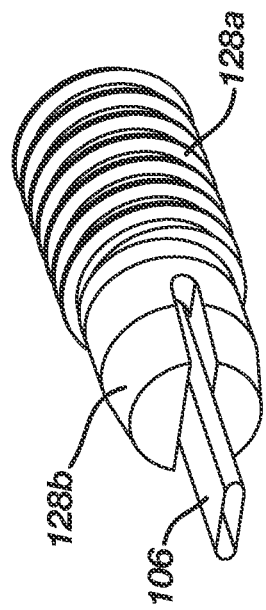
FIG. 7G is a perspective view of an engagement between a component of a delivery device and a flexible segment of an example implant, such as that shown in FIG. 1, according to aspects of the present invention.
Figure 7D:
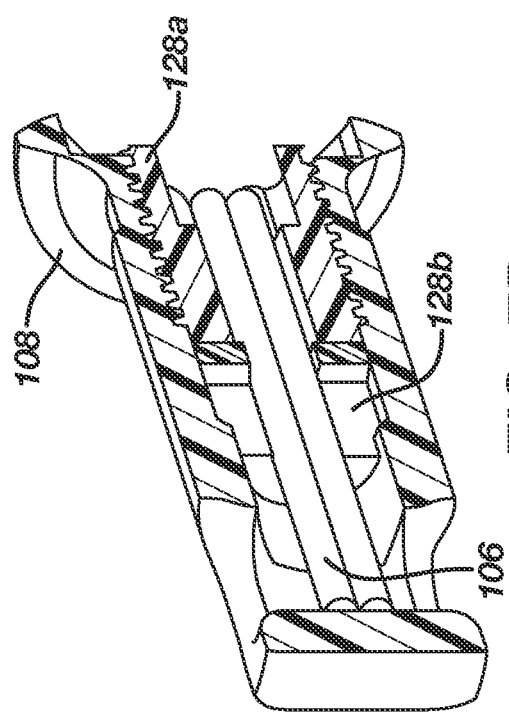
FIG. 7D is a cross-sectional view of an engagement between a second anchor and a flexible segment of an example implant, such as that shown in FIG. 1, according to aspects of the present invention.
Figure 7F:
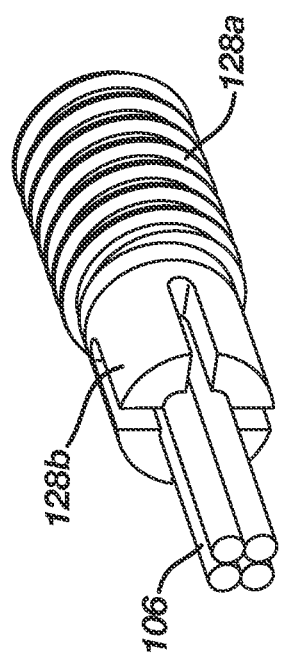
FIG. 7F is a perspective view of an engagement between a component of a delivery device and a flexible segment of an example implant, such as that shown in FIG. 1, according to aspects of the present invention.

FIGS. 7A-7G provide examples of engagements between the second anchor 108 and the flexible segment 106. As shown, the third handle 128 may include an internal shaft 128a and a locking component 128b. As the third handle 128 is rotated, as discussed above and particularly shown in FIGS. 7A-7B, the internal shaft 128a may be rotated thereby moving the locking component 128b in a distal direction 12 and engaging the locking component 128b with the flexible segment 106 and the second anchor 108, and thereby attaching the flexible segment 106 to the second anchor 108. As shown, the flexible segment 106 may be configured in one of many different shapes, arrangements, configurations, etc., depending on the selected shape and/or configuration of the second anchor 108 and/or the delivery device 120. For example, FIG. 7F illustrates a flexible segment 106 having four individual suture strands, while FIG. 7G (FIG. 7E showing a cross-sectional view thereof) illustrates a flexible segment 106 having a single and flatter suture strand. FIG. 7D shows a cross-sectional and perspective view of how, for example, the flexible segment 106, internal shaft 128a, and locking component 128b of FIG. 7F might engage with second anchor 108.

FIGS. 8A-8B provide an example of another system 200 for the approximation and tensioning of two bones, such as the tibia and fibula bones. As with system 100, discussed above, system 200 may include an implant 102, such as that shown in FIG. 1, and a delivery device 220. Delivery device 220 may include a first handle 222, a second handle 226, and a third handle 224.

As particularly shown in FIG. 8B, and further discussed below, the second handle 226 may include a suture carriage 226a disposed within the delivery device 220 and configured to rotate and move along the longitudinal axis of the delivery device 220 as the second handle 226 is rotated. As such, the suture carriage 226a may aid in adjusting the tension of the flexible segment 106, as further discussed below.

As also particularly shown in FIG. 8B, the third handle 224 may include an internal shaft 224a, whereby rotation of the third handle 224 is configured to rotate the internal shaft 224a to engage the locking component 228 (FIG. 9D) with the second anchor 108 and the flexible segment 106, as further discussed below.

FIGS. 9A-9E provide an example method for delivering an implant 102 into two bones, such as the tibia and fibula bones, using delivery device 220.

As shown in FIG. 9A, the first, second, and third handles 222, 226, 224 may be simultaneously rotated, thereby facilitating the insertion of the first anchor 104 into the first hole 110 of the first bone 112.

As shown in FIG. 9B, once the first anchor 104 has been inserted into and anchored in the first bone 112, the third handle 224 may be removed from the delivery device 220, thereby enabling the second handle 226 to be independently rotated to thereby increase tension on the flexible segment 106 by pulling one or more proximal ends 106a of the flexible segment 106 in a proximal direction 10. As discussed above with respect to FIG. 8B, as the second handle 226 is rotated, the internal suture carriage 226a may move along the longitudinal axis of the delivery device 220, thereby aiding in adjusting the tension on the flexible segment 106.

Figure 9C:
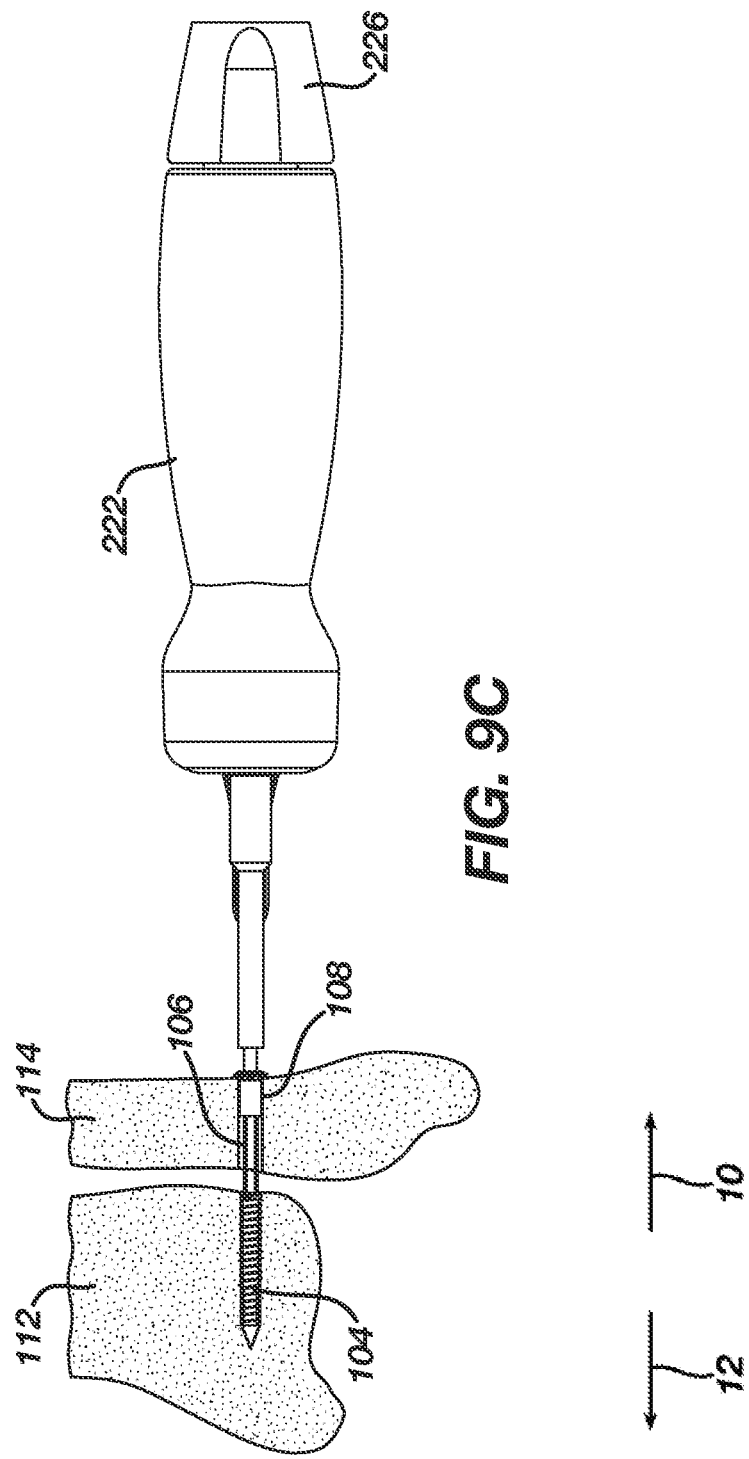
FIG. 9C is a cross-sectional view of a tibia and fibula showing an example step of an example method for installing an implant, such as that shown in FIG. 1, according to aspects of the present invention.
Figure 9D:
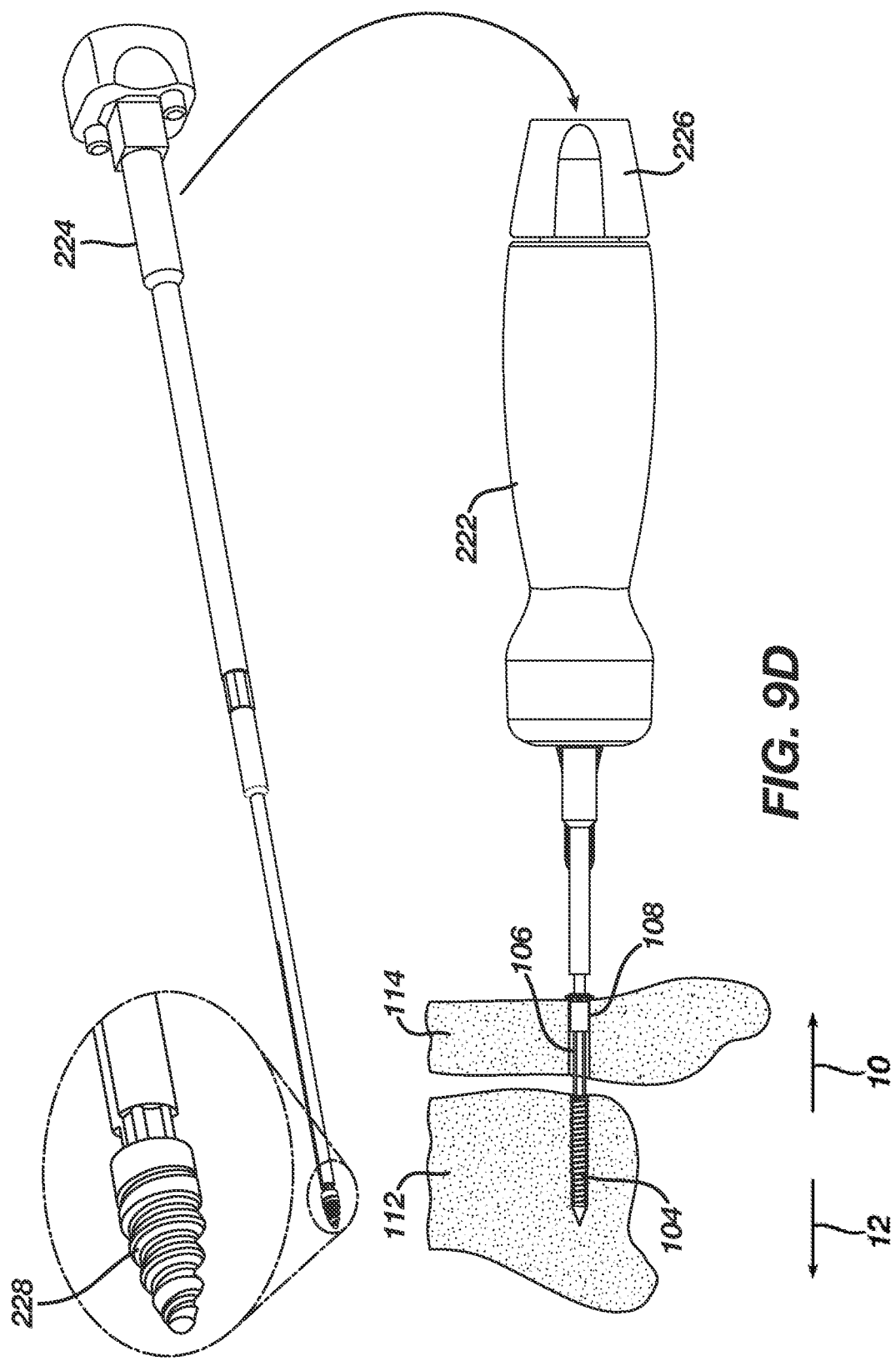
FIG. 9D is a cross-sectional view of a tibia and fibula showing an example step of an example method for installing an implant, such as that shown in FIG. 1, according to aspects of the present invention.
Figure 9E:
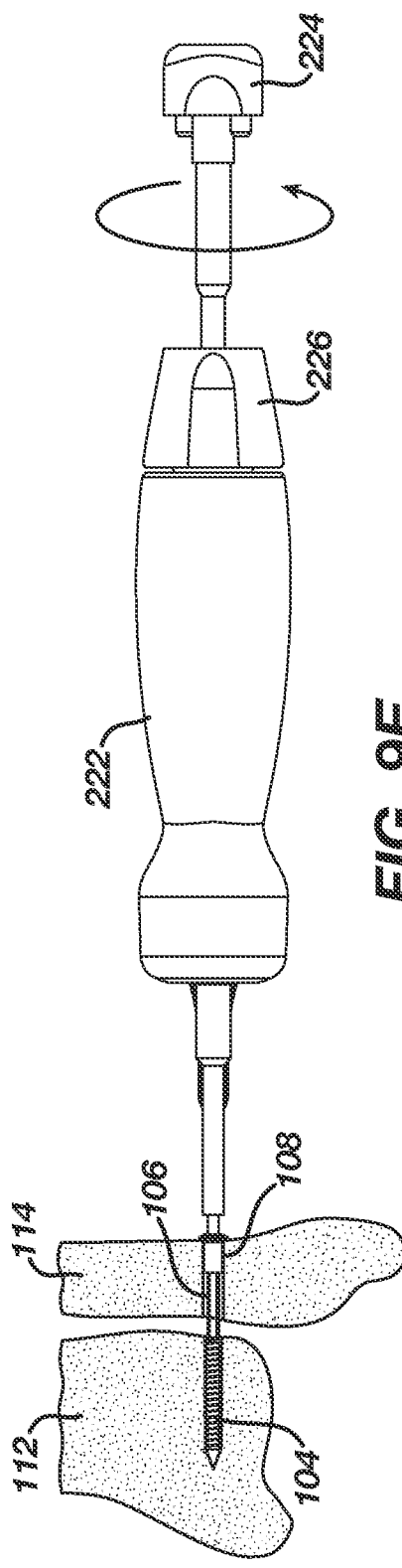
FIG. 9E is a cross-sectional view of a tibia and fibula showing an example step of an example method for installing an implant, such as that shown in FIG. 1, according to aspects of the present invention.
Figure 10:
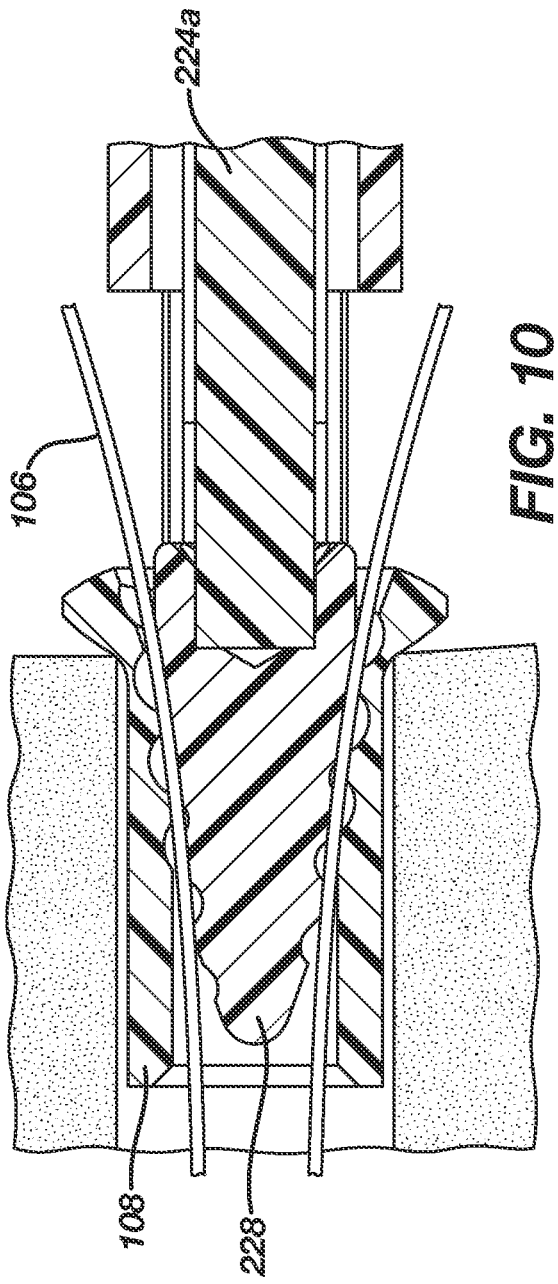
FIG. 10 is a cross-sectional view of an engagement between a second anchor and a flexible segment of an example implant, such as that shown in FIG. 1, according to aspects of the present invention.

As shown in FIGS. 9C-9E, the third handle 224 may then be re-attached to the delivery device 220. The third handle 224 may include an internal shaft 224a (FIGS. 8B and 10) and a locking component 228 (FIGS. 9D and 10). Rotation of the third handle 224 (FIG. 9E) may be configured to rotate the internal shaft 224a to engage the locking component 228 with the flexible segment 106 and the second anchor 108, thereby attaching the flexible segment 106 to the second anchor 108, as particularly shown in FIG. 10.

FIG. 11 provides a flowchart of an example method 300 for syndesmosis tensioning.

In block 302, the method may include delivering, via a first handle (e.g., 122, 222) and a removeable driver (e.g., 124, 224) of a delivery device (e.g., 120, 220), a first anchor (e.g., 104) into a first bone (e.g., 112), wherein the first anchor engages with a distal end of a flexible segment (e.g., 106).

In block 304, the method may include disengaging the removeable driver from the delivery device, thereby exposing the flexible segment, for example, as discussed with respect to FIGS. 4 and 9B.

In block 306, the method may include adjusting, via a second handle (e.g., 126, 226) of the delivery device, tension of the flexible segment by pulling one or more proximal ends of the flexible segment in a proximal direction.

In block 308, the method may include delivering, via a third handle (e.g., 128, 224) of the delivery device, a second anchor (e.g., 108) into a second bone (e.g., 114).

In block 310, the method may include attaching, via the third handle (e.g., 128, 224) of the delivery device, the flexible segment to the second anchor.

Figure 12:
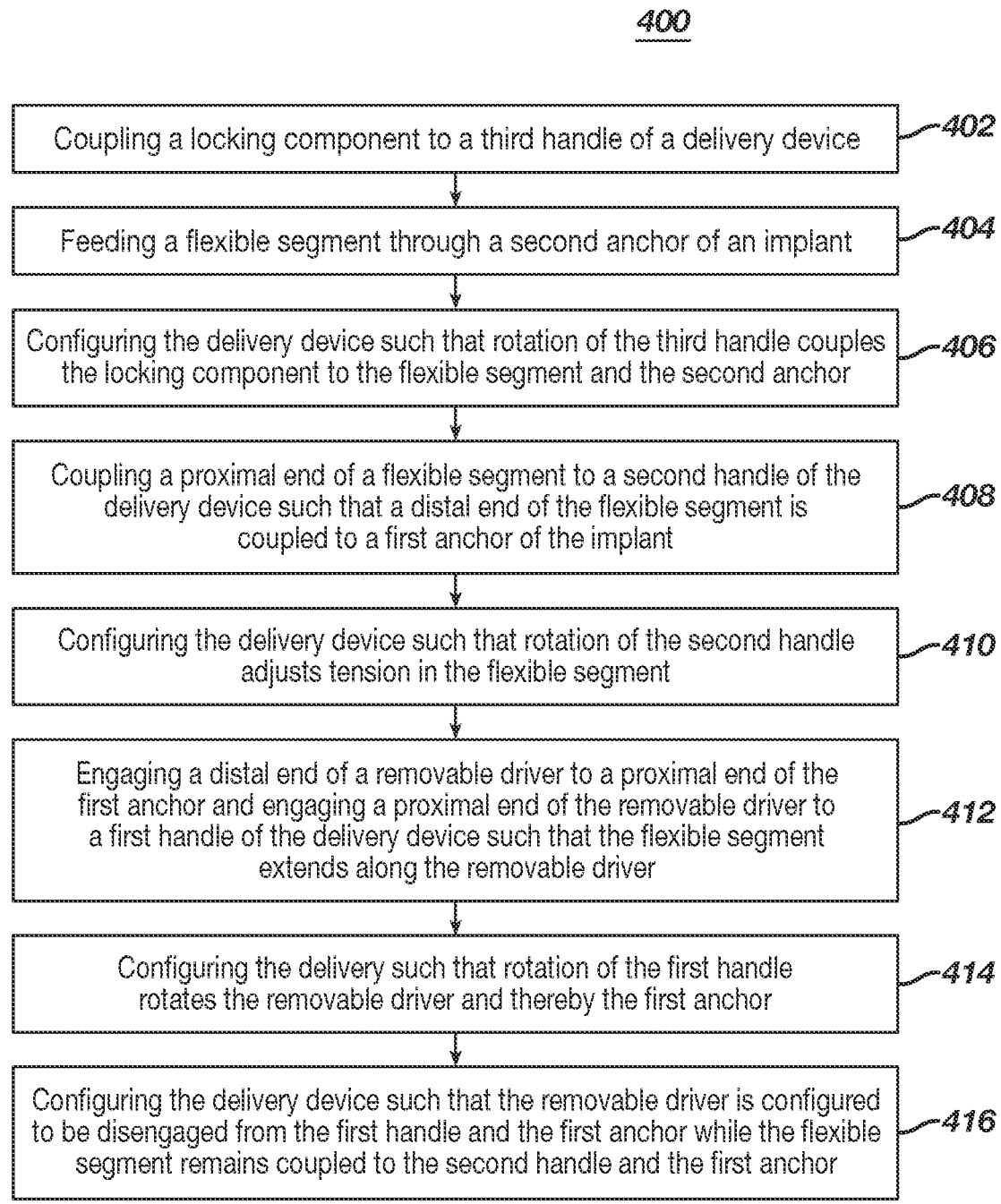
FIG. 12 is a flowchart of an example method for providing syndesmosis tensioning, according to aspects of the present invention.

FIG. 12 provides a flowchart of an example method 400 for constructing a system for syndesmosis tensioning.

In block 402, the method may include coupling a locking component (e.g., 128a) to a third handle (e.g., 128) of a delivery device (e.g., 120). For example, as shown in FIG. 7A, locking component 128a may be coupled or attached to the internal shaft 128a of the third handle 128.

In block 404, the method may include feeding a flexible segment through a second anchor of an implant. For example, as discussed herein, one or more proximal ends of the flexible segment may extend from a proximal end of a first anchor, through a second anchor, and past the proximal end of the second anchor such that the delivery device can adjust tension of the flexible segment by moving the proximal ends in a proximal direction.

In block 406, the method may include configuring the delivery device such that rotation of the third handle couples the locking component to the flexible segment and the second anchor, such as discussed above with respect to FIG. 6.

In block 408, the method may include coupling a proximal end of a flexible segment to a second handle of the delivery device such that a distal end of the flexible segment is coupled to a first anchor of the implant. For example, a distal end 106b of flexible segment 106 may be coupled to the first anchor 104, e.g., as discussed with respect to FIG. 2, while a proximal end 106a of flexible segment 106 may be coupled to a second handle 126, e.g., via extensions 130.

In block 410, the method may include configuring the delivery device such that rotation of the second handle adjusts tension in the flexible segment, such as discussed above with respect to FIG. 5.

In block 412, the method may include engaging a distal end of a removable driver to a proximal end of the first anchor and engaging a proximal end of the removable driver to a first handle of the delivery device such that the flexible segment extends along the removable driver. For example, as shown in FIG. 3, a distal end of removeable driver 124 may be engaged with a proximal end of first anchor 104, while a proximal end of removeable driver 124 is engaged with first handle 122. As shown in FIG. 4, once the removeable driver 124 is disengaged, flexible segment 106 is exposed, extending between the first and second anchors 104, 108.

In block 414, the method may include configuring the delivery device such that rotation of the first handle rotates the removable driver and thereby the first anchor, for example as discussed above with respect to FIG. 3.

In block 416, the method may include configuring the delivery device such that the removable driver is configured to be disengaged from the first handle and the first anchor while the flexible segment remains coupled to the second handle and the first anchor, for example as discussed above with respect to FIG. 4.

The descriptions contained herein are examples of embodiments of the invention and are not intended in any way to limit the scope of the invention. As described herein, the invention contemplates many variations and modifications of structures and methods, including alternative materials, alternative configurations of component parts, and alternative method steps. Modifications and variations apparent to those having skill in the pertinent art according to the teachings of this disclosure are intended to be within the scope of the claims which follow.

The disclosed technology described herein can be further understood according to the following clauses.

Clause 1. A system for the approximation of two bones, the system comprising: an implant comprising a first anchor, a flexible segment, and a second anchor, the first anchor comprising a distal end configured for insertion into a first hole in a first bone, the second anchor being configured to engage with a second bone, and the flexible segment extending between the first and second anchors; and a delivery device configured to engage the implant with the first and second bones, the delivery device comprising: a removable driver configured to engage the first anchor to facilitate insertion of the first anchor into the first hole; a first handle configured to engage the removeable driver to facilitate insertion of the first anchor into the first hole by the removable driver; a second handle coupled to the first handle and configured, with the removable driver disengaged from the first handle and first anchor, to increase tension on the flexible segment by pulling one or more proximal ends of the flexible segment in a proximal direction; and a third handle configured to engage the second anchor with the second bone and to attach the flexible segment to the second anchor.

Clause 2. The system of clause 1, wherein the third handle is the removable driver.

Clause 3. The system of clause 1, wherein the delivery device further comprises one or more extensions configured to engage with the one or more proximal ends of the flexible segment, and wherein rotation of the second handle is configured to move the one or more extensions proximally along a length of the delivery device thereby increasing the tension on the flexible segment.

Clause 4. The system of clause 1, wherein the second handle is rotatable independent of the first handle.

Clause 5. The system of clause 1, wherein the delivery device further comprises a slider configured to slide along a length of the removeable driver thereby enabling the removeable driver to disengage from the delivery device.

Clause 6. The system of clause 1, wherein rotation of the first handle is configured to cause rotation of the removable driver and the first anchor, with the removable driver engaged to the first handle and first anchor.

Clause 7. The system of clause 1, wherein the third handle comprises an internal shaft and a locking component.

Clause 8. The system of clause 7, wherein rotation of the third handle is configured to rotate the internal shaft to engage the locking component with the flexible segment and the second anchor, thereby attaching the flexible segment to the second anchor.

Clause 9. A method for the approximation of two bones, the method comprising: delivering, via a first handle and a removeable driver of a delivery device, a first anchor into a first bone, wherein the first anchor engages with a distal end of a flexible segment; disengaging the removeable driver from the delivery device, thereby exposing the flexible segment; adjusting, via a second handle of the delivery device, tension of the flexible segment by pulling one or more proximal ends of the flexible segment in a proximal direction; delivering, via a third handle of the delivery device, a second anchor into a second bone; and attaching, via the third handle of the delivery device, the flexible segment to the second anchor.

Clause 10. The method of clause 9, wherein the third handle is the removable driver.

Clause 11. The method of clause 9, wherein the one or more proximal ends of the flexible segment are attached to one or more extensions disposed on the delivery device, and wherein adjusting the tension of the flexible segment is conducted by moving the one or more extensions proximally along a length of the delivery device.

Clause 12. The method of clause 9, wherein disengaging the removeable driver from the delivery device comprises moving a slider along a length of the removeable driver.

Clause 13. The method of clause 9, wherein the third handle comprises an internal shaft and a locking component.

Clause 14. The method of clause 13, wherein rotation of the third handle is configured to rotate the internal shaft to engage the locking component with the flexible segment and the second anchor, thereby attaching the flexible segment to the second anchor.

Clause 15. The method of clause 9, wherein the delivery device comprises a force gauge, and wherein adjusting the tension of the flexible segment comprises rotating the second handle of the delivery device thereby providing, via the force gauge, an indication of the tensile force placed on the flexible segment.

Clause 16. A method of constructing a system for approximation of two bones, the method comprising: coupling a locking component to a third handle of a delivery device; feeding a flexible segment through a second anchor of an implant; configuring the delivery device such that rotation of the third handle couples the locking component to the flexible segment and the second anchor; coupling a proximal end of a flexible segment to a second handle of the delivery device such that a distal end of the flexible segment is coupled to a first anchor of the implant; configuring the delivery device such that rotation of the second handle adjusts tension in the flexible segment; engaging a distal end of a removeable driver to a proximal end of the first anchor and engaging a proximal end of the removable driver to a first handle of the delivery device such that the flexible segment extends along the removable driver; configuring the delivery device such that rotation of the first handle rotates the removable driver and thereby the first anchor; and configuring the delivery device such that the removable driver is configured to be disengaged from the first handle and the first anchor while the flexible segment remains coupled to the second handle and the first anchor.

Clause 17. The method of clause 16, wherein coupling the proximal end of the flexible segment to the second handle comprises attaching the proximal end to one or more extensions disposed on the delivery device.

Clause 18. The method of clause 17, wherein adjusting the tension in the flexible segment is conducted by moving the one or more extensions proximally along a length of the delivery device.

Clause 19. The method of clause 16, wherein the removeable driver is configured to be disengaged from the first handle by moving a slider along a length of the removeable driver.

Clause 20. The method of clause 16, wherein the third handle comprises an internal shaft, and wherein rotation of the third handle rotates the internal shaft to couple the locking component to the flexible segment and the second anchor.

Clause 21. A method of constructing a system for approximation of two bones, the method comprising: coupling a locking component to a third handle of a delivery device; feeding a flexible segment through a second anchor of an implant; configuring the delivery device such that rotation of the third handle couples the locking component to the flexible segment and the second anchor; coupling a proximal end of a flexible segment to a second handle of the delivery device such that a distal end of the flexible segment is coupled to a first anchor of the implant; configuring the delivery device such that rotation of the second handle adjusts tension in the flexible segment; engaging a distal end of the third handle to a proximal end of the first anchor and engaging the third handle to the second handle and a first handle of the delivery device such that the flexible segment extends along the third handle; configuring the delivery device such that rotation of the third handle rotates the first anchor; and configuring the delivery device such that the third handle is configured to be disengaged from the delivery device and the first anchor while the flexible segment remains coupled to the second handle and the first anchor.

What is claimed is:

1. A system for approximation of two bones, the system comprising:
   an implant comprising a first anchor, a flexible segment, and a second anchor, the first anchor comprising a distal end configured for insertion into a first hole in a first bone, the second anchor being configured to engage with a second bone, and the flexible segment extending between the first and second anchors; and
   a delivery device configured to engage the implant with the first and second bones, the delivery device comprising:
      a removable driver configured to engage the first anchor to facilitate insertion of the first anchor into the first hole;
      a first handle configured to engage the removeable driver to facilitate insertion of the first anchor into the first hole by the removable driver;
      a second handle coupled to the first handle and configured, with the removable driver disengaged from the first handle and first anchor, to increase tension on the flexible segment by pulling one or more proximal ends of the flexible segment in a proximal direction; and
      a third handle configured to engage the second anchor with the second bone and to attach the flexible segment to the second anchor.

2. The system of claim 1, wherein the delivery device further comprises one or more extensions configured to engage with the one or more proximal ends of the flexible segment, and wherein rotation of the second handle is configured to move the one or more extensions proximally along a length of the delivery device thereby increasing the tension on the flexible segment.

3. The system of claim 1, wherein the second handle is rotatable independent of the first handle.

4. The system of claim 1, wherein the delivery device further comprises a slider configured to slide along a length of the removeable driver thereby enabling the removeable driver to disengage from the delivery device.

5. The system of claim 1, wherein rotation of the first handle is configured to cause rotation of the removable driver and the first anchor, with the removable driver engaged to the first handle and first anchor.

6. The system of claim 1, wherein the third handle comprises an internal shaft and a locking component.

7. The system of claim 6, wherein rotation of the third handle is configured to rotate the internal shaft to engage the locking component with the flexible segment and the second anchor, thereby attaching the flexible segment to the second anchor.

8. A method for approximation of two bones, the method comprising:
   delivering, via a first handle and a removeable driver of a delivery device, a first anchor into a first bone,
      wherein the first anchor engages with a distal end of a flexible segment;
   disengaging the removeable driver from the delivery device, thereby exposing the flexible segment;
   adjusting, via a second handle of the delivery device, tension of the flexible segment by pulling one or more proximal ends of the flexible segment in a proximal direction;
   delivering, via a third handle of the delivery device, a second anchor into a second bone; and
   attaching, via the third handle of the delivery device, the flexible segment to the second anchor.

9. The method of claim 8, wherein the one or more proximal ends of the flexible segment are attached to one or more extensions disposed on the delivery device, and wherein adjusting the tension of the flexible segment is conducted by moving the one or more extensions proximally along a length of the delivery device.

10. The method of claim 8, wherein disengaging the removeable driver from the delivery device comprises moving a slider along a length of the removeable driver.

11. The method of claim 8, wherein the third handle comprises an internal shaft and a locking component.

12. The method of claim 11, wherein rotation of the third handle is configured to rotate the internal shaft to engage the locking component with the flexible segment and the second anchor, thereby attaching the flexible segment to the second anchor.

13. The method of claim 8, wherein the delivery device comprises a force gauge, and wherein adjusting the tension of the flexible segment comprises rotating the second handle of the delivery device thereby providing, via the force gauge, an indication of the tensile force placed on the flexible segment.

14. A method of constructing a system for approximation of two bones, the method comprising:
   coupling a locking component to a third handle of a delivery device;
   feeding a flexible segment through a second anchor of an implant;
   configuring the delivery device such that rotation of the third handle couples the locking component to the flexible segment and the second anchor;
   coupling a proximal end of the flexible segment to a second handle of the delivery device such that a distal end of the flexible segment is coupled to a first anchor of the implant;

configuring the delivery device such that rotation of the second handle adjusts tension in the flexible segment;

engaging a distal end of a removable driver to a proximal end of the first anchor and engaging a proximal end of the removable driver to a first handle of the delivery device such that the flexible segment extends along the removable driver;

configuring the delivery device such that rotation of the first handle rotates the removable driver and thereby the first anchor; and configuring the delivery device such that the removable driver is configured to be disengaged from the first handle and the first anchor while the flexible segment remains coupled to the second handle and the first anchor.

15. The method of claim 14, wherein coupling the proximal end of the flexible segment to the second handle comprises attaching the proximal end to one or more extensions disposed on the delivery device.

16. The method of claim 15, wherein adjusting the tension in the flexible segment is conducted by moving the one or more extensions proximally along a length of the delivery device.

17. The method of claim 14, wherein the removeable driver is configured to be disengaged from the first handle by moving a slider along a length of the removeable driver.

18. The method of claim 14, wherein the third handle comprises an internal shaft, and wherein rotation of the third handle rotates the internal shaft to couple the locking component to the flexible segment and the second anchor.

* * * * *